(12) United States Patent
Achmüller et al.

(10) Patent No.: US 10,947,287 B2
(45) Date of Patent: Mar. 16, 2021

(54) DNA CODING SEQUENCE FOR HUMAN G-CSF

(71) Applicant: Sandoz AG, Basel (CH)

(72) Inventors: Clemens Achmüller, Kundl (AT); Johann Holzmann, Kundl (AT); Stefan Hutwimmer, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 15/767,221

(22) PCT Filed: Oct. 19, 2016

(86) PCT No.: PCT/EP2016/075039
§ 371 (c)(1),
(2) Date: Apr. 10, 2018

(87) PCT Pub. No.: WO2017/067958
PCT Pub. Date: Apr. 27, 2017

(65) Prior Publication Data
US 2019/0071481 A1  Mar. 7, 2019

(30) Foreign Application Priority Data
Oct. 19, 2015  (EP) .................................... 15190353

(51) Int. Cl.
*C07K 14/535* (2006.01)
*C12N 15/64* (2006.01)
*C12N 15/74* (2006.01)

(52) U.S. Cl.
CPC ............ *C07K 14/535* (2013.01); *C12N 15/64* (2013.01); *C12N 15/74* (2013.01)

(58) Field of Classification Search
CPC ...... C07K 14/535; C12N 15/85; C12N 15/63; C12N 1/14; C12N 1/16; C12P 1/02; C12P 19/34
See application file for complete search history.

(56) References Cited

U.S. PATENT DOCUMENTS

| 4,810,643 | A | 3/1989 | Souza |
| 6,627,186 | B1 | 9/2003 | Dahiyat et al. |
| 2003/0166527 | A1 | 9/2003 | Sarkar et al. |

FOREIGN PATENT DOCUMENTS

| WO | 8701132 | 2/1987 |
| WO | 9853072 | 11/1998 |

OTHER PUBLICATIONS

SMS web site—back translation of the protein of SEQ ID No. 8 (Jun. 9, 2020) (Year: 2020).*
Search Report and Written Opinion for PCT/EP2016/075039, dated Apr. 27, 2017, 12 pages.

* cited by examiner

*Primary Examiner* — Elly-Gerald Stoica
(74) *Attorney, Agent, or Firm* — Luedeka Neely Group, P.C.

(57) ABSTRACT

The present invention relates in general to a nucleic acid encoding human granulocyte-colony stimulating factor (G-CSF), wherein the first leucine residue occurring on the N-terminal end of the encoded G-CSF is encoded by a codon other than the CTG/CUG codon, and wherein the nucleic acid does neither comprise the nucleic acid sequence according to SEQ ID NO: 1, nor according to SEQ ID NO: 2, nor according to SEQ ID NO: 3, nor according to SEQ ID NO: 4. The present invention also relates to a nucleic acid 100% complementary to the aforementioned nucleic acid, as well as to vectors and host cells comprising the aforementioned nucleic acids. Finally, the present invention relates to methods for producing human G-CSF using these nucleic acids, vectors and/or host cells and resulting G-CSF compositions.

Figure 1:
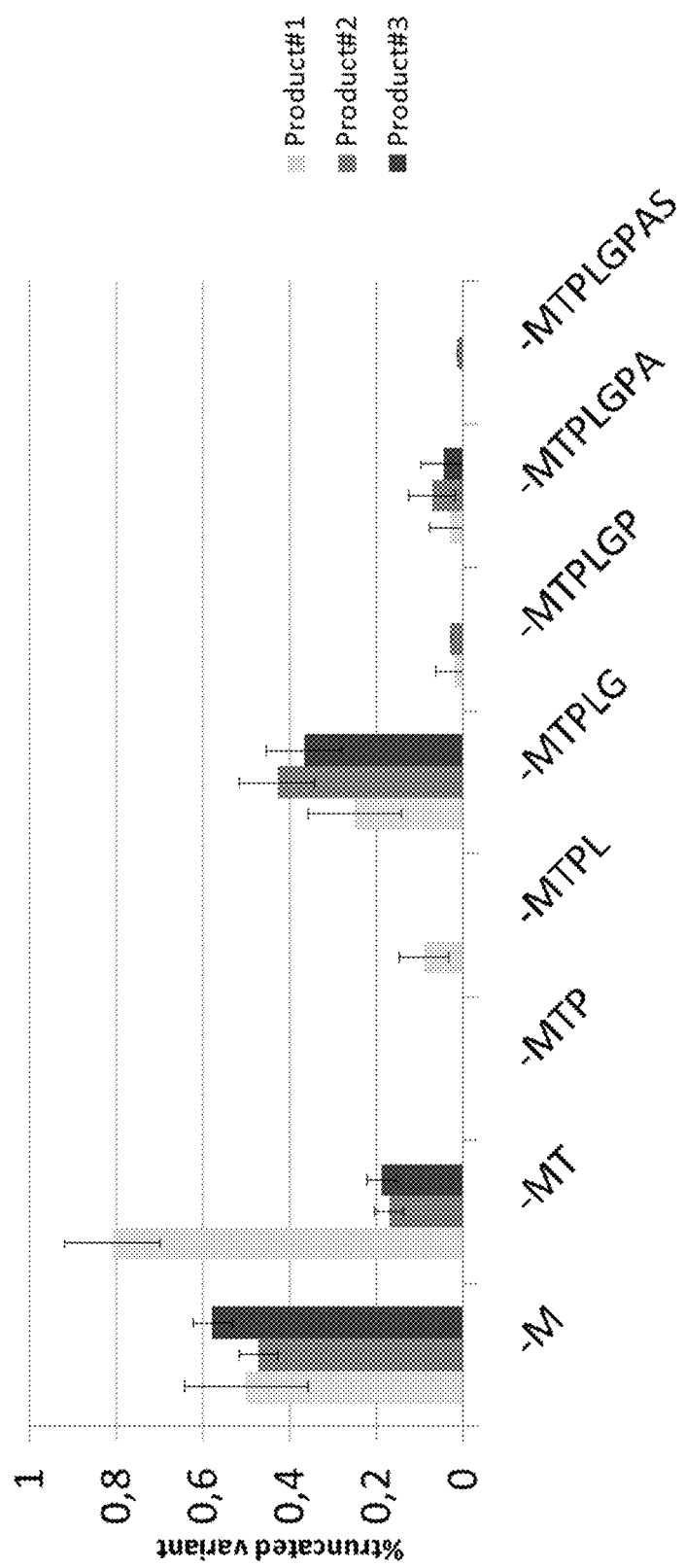

9 Claims, 3 Drawing Sheets
Specification includes a Sequence Listing.

DNA CODING SEQUENCE FOR HUMAN G-CSF

This application is a Section 371 national phase entry of PCT application PCT/EP2016/075039, filed Oct. 19, 2016. This application also claims the benefit of the earlier filing date of European patent application 15190353.1, filed Oct. 19, 2015.

This application contains a Sequence Listing which has been submitted electronically in ASCII format and is herein incorporated by reference. The ASCII file, created on Mar. 6, 2018, is named 73588us-topto-20180410-HEX-009_ST25, and is 22,217 bytes in size.

The present invention relates to a nucleic acid encoding human granulocyte-colony stimulating factor (G-CSF), wherein the first leucine residue occurring on the N-terminal end of the encoded G-CSF is encoded by a codon other than the CTG/CUG codon, and wherein the nucleic acid does neither comprise the nucleic acid sequence according to SEQ ID NO: 1, nor according to SEQ ID NO: 2, nor according to SEQ ID NO: 3, nor according to SEQ ID NO: 4. The present invention also relates to a nucleic acid 100% complementary to the aforementioned nucleic acid, as well as to vectors and host cells comprising the aforementioned nucleic acids. Finally, the present invention relates to methods for producing human G-CSF using these nucleic acids, vectors and/or host cells and resulting G-CSF compositions.

Granulocyte colony stimulating factor (G-CSF) is a polypeptide based hormone of mammals. It is a cytokine and stimulates inter alia the production of granulocytes. G-CSF also stimulates the survival, proliferation, differentiation, and function of neutrophil precursors and mature neutrophils. The natural human glycoprotein exists in two forms, a (more active) 174- and (less active) 177-amino-acid-long polypeptide.

The 174 amino acid long version of human G-CSF (hG-CSF) has been used for several pharmaceutical applications. In oncology and hematology, hG-CSF is used with certain cancer patients to accelerate recovery from neutropenia (i.e. abnormally low number of neutrophils) after chemotherapy. G-CSF is also used to increase the number of hematopoietic stem cells in the blood of the donor before collection for use in hematopoietic stem cell transplantation. Several other clinical applications are contemplated as well.

U.S. Pat. No. 4,810,643 disclosed the recombinant expression of hG-CSF in prokaryotic or eukaryotic host cells. The resulting protein products displayed the physical and immunological properties and in vitro biological activities of isolates of hG-CSF derived from natural sources. G-CSF was first marketed by Amgen with the brand name Neupogen®. In 2014, the sales of Neupogen® amounted to about 1.2 billion US dollar worldwide. Several biosimilar versions are also available. The recombinant human G-CSF, synthesized in an *E. coli* expression system, is called filgrastim. The structure of filgrastim differs slightly from the structure of the natural glycoprotein, because it exhibits an additional methionine residue at the N-terminus and is not glycosylated. A pegylated version of filgrastim is also marketed. hG-CSF expressed in a mammalian expression system (lenograstim), such as CHO cells, is indistinguishable from the 174-amino acid long natural (i.e. non-recombinant) human G-CSF.

In order to meet the high regulatory standards for biologics and biosimilars, the biotechnological production of G-CSF requires a high level of purity. However, one problem arising in the biotechnological production of G-CSF is N-terminal truncation. G-CSF contains a non-structured, flexible N-terminal region of about 10 amino acids length which is prone to degradation. The amount of respective truncation products must be reduced to meet the purity specifications for the pharmaceutical product. Said purification process in turn brings about a reduction in yield and concomitantly an increase in production costs. Characterization of three commercially available Filgrastim products reveals still residual presence of said truncation variants (see FIG. 1).

Given the loss in yield and the risk of failing regulatory requirements, there is thus a need in the art to establish new means for reducing said loss in yield and risk. It was thus the object of the present invention to provide a means for reducing the amount of N-terminal truncation products of biotechnologically produced G-CSF.

This problem is solved by the subject-matter as set forth below and in the appended claims.

In the following a brief description of the appended figures will be given. The figures are intended to illustrate the present invention in more detail. However, they are not intended to limit the scope of the invention to these specific examples.

FIG. 1: illustrates the results of three commercially available Filgrastim products with respect to presence of N-terminally truncated variants of G-CSF in the product. The analysis revealed that even in the final products there were still truncated versions of recombinant G-CSF present, which lacked up to 8 amino acids at the N-terminus.

Figure 2:
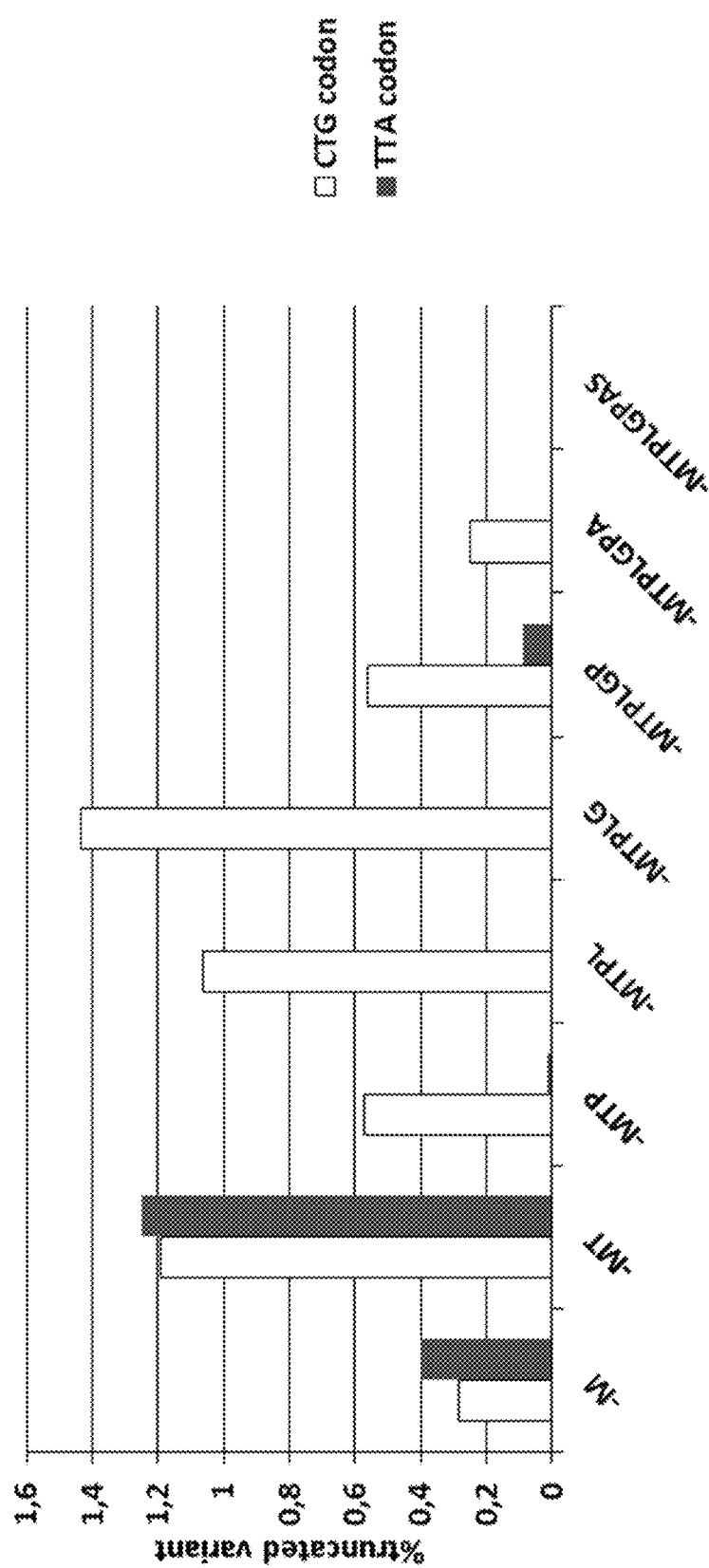

FIG. 2: is a graph comparing the abundance of individual species of N-terminally truncated versions (lacking the first 1 to 8 amino acids) of recombinant G-CSF depending on the leucine codon used at position 4 (CTG or TTA). The results are based on LC-MS-analysis.

Figure 3:
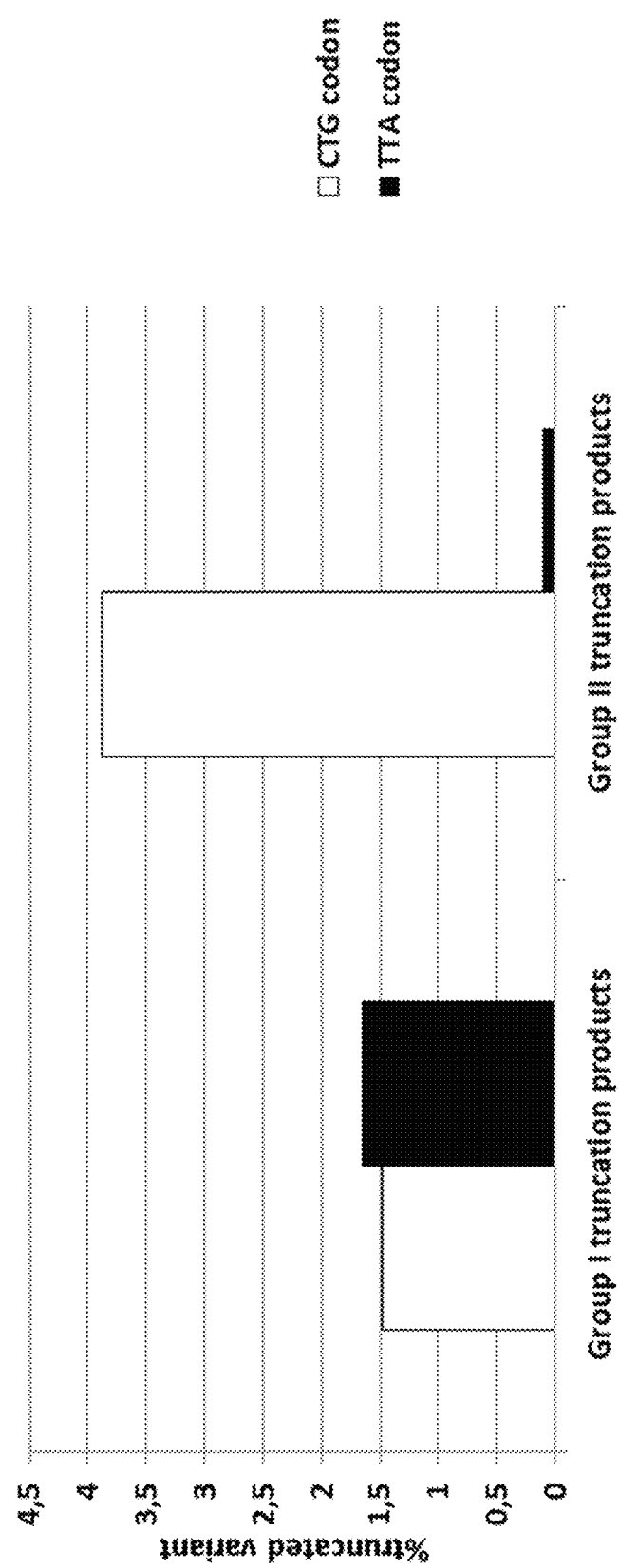

FIG. 3: is a graph comparing the abundance of N-terminally truncated versions lacking the first 1 or 2 amino acids of recombinant G-CSF (group I truncations) vs. N-terminally truncated versions lacking the first 3 to 7 amino acids of recombinant G-CSF (group II truncations) or even lacking 8 amino acids of recombinant G-CSF, either with the standard CTG codon or a TTA codon.

In a first aspect the present invention relates to a nucleic acid encoding human granulocyte colony stimulating factor (G-CSF), wherein the first leucine residue occurring on the N-terminal side of the encoded human G-CSF is encoded by a codon other than the CTG/CUG codon, and wherein the nucleic acid does neither comprise the nucleic acid sequence according to SEQ ID NO: 1, nor according to SEQ ID NO: 2 (RNA equivalent of SEQ ID NO: 1), nor according to SEQ ID NO: 3, nor according to SEQ ID NO: 4 (RNA equivalent of SEQ ID NO: 3). The leucine residue is encoded by a codon other than the CTG codon, if the nucleic acid is DNA, or other than the CUG codon, if the nucleic acid is RNA.

The inventors of the present invention have surprisingly found that using an alternative codon for said leucine residue dramatically reduces the proportion of N-terminal truncation products of G-CSF. In particular, such alternative codon reduces the level of those truncation products in which the first 3 to 7 amino acids of recombinant G-CSF (SEQ ID NO: 5) are absent (group II truncations). Thus, any form of G-CSF exhibiting said leucine residue may be produced recombinantly with reduced levels of truncation products, if such alternative codon is used.

The term "granulocyte colony stimulating factor", or G-CSF, as used herein, encompasses all forms of human G-CSF known or conceivable for a person skilled in the art. In particular, the term encompasses all allelic variants. The term encompasses recombinant G-CSF (i.e. with methionine at the N-terminus) as well as natural G-CSF (i.e. without methionine at the N-terminus). The term "G-CSF" does also encompass mutated versions of naturally occurring G-CSF, with the proviso that they still exhibit the flexible N-terminal region of about 10 amino acids length of G-CSF and in particular the required leucine residue on the N-terminal end. Most preferably, such mutated versions do still exhibit the biological activity of G-CSF. Preferably, such mutated versions of naturally occurring G-CSF are at least 30, at least 40, at least 50, at least 60, at least 70, at least 80, at least 90, at least 100, at least 110, at least 120, at least 130, at least 140, at least 150 or more than 160 amino acids long. The nucleic acid encoding granulocyte colony stimulating factor (G-CSF) may also encode a G-CSF precursor exhibiting a signal peptide at the N-terminus which may posttranslationally be proteolytically cleaved. The nucleic acid encoding granulocyte colony stimulating factor (G-CSF) may also encode fusion proteins comprising G-CSF on the one hand and one or more further fusion partners on the other hand. Particularly preferred are fusion proteins, in which G-CSF forms the N-terminal part of the fusion protein. Examples for potential fusion partners are for instance conventionally used tags, such as His-tags or detectable markers such as GFP. The eventually produced G-CSF may be glycosylated, pegylated, both (i.e. is glycosylated and pegylated) or none of it (i.e. is neither glycosylated nor pegylated). A particularly preferred G-CSF is G-CSF according to SEQ ID NO: 5.

"The first leucine residue occurring on the N-terminal end", as used herein, is necessarily a relative expression. The exact position of the leucine residue cannot be defined more precisely given the fact that the term "G-CSF" as used herein encompasses various entities, not all of which have the identical length and/or sequence of amino acid residues. The term "first leucine residue occurring on the N-terminal end" refers typically to the leucine residue occurring at position 3 of the G-CSF sequence (L3), see for example natural human G-CSF (SEQ ID NO: 6). In recombinant G-CSF, where an additional methionine residue is present at the N-terminus, it corresponds to position 4 (see SEQ ID NO: 5). In G-CSF variants with additional amino acid residues N-terminal of the actual G-CSF sequence, the absolute position vis-à-vis the N-terminal end may be different. For example, in the non-cleaved G-CSF precursor including the signal peptide, it corresponds to position 33 (see for example SEQ ID NO: 7), because the term refers to the first leucine residue of G-CSF and not to the first leucine of the precursor sequence. In fusion proteins comprising G-CSF, in which G-CSF does not form the most N-terminal portion, the absolute position of the leucine residue will likewise be distinct and depends on the position of G-CSF within the fusion. However, a person skilled in the art will be readily capable of determining the position of the G-CSF sequence within such fusion protein and then the position of the leucine residue in question, e.g. by performing respective alignments of the sequence of the fusion protein and, e.g., the natural G-CSF sequence.

Preferably, the nucleic acid according to the present invention encodes human granulocyte-colony stimulating factor (hG-CSF), in particular hG-CSF according to SEQ ID NO: 8, wherein the first leucine residue occurring on the N-terminal end is L4 of SEQ ID NO: 8. SEQ ID NO: 8 represents the human G-CSF sequence, wherein the first amino acid residue of SEQ ID NO: 8 is either absent (natural hG-CSF) or methionine (recombinant hG-CSF). A particularly preferred form of G-CSF is recombinant human G-CSF according to SEQ ID NO: 5.

The term "nucleic acid", as used herein, refers to a chain of nucleic acid residues, either single stranded or double stranded. The nucleic acid of the present invention may be DNA or RNA, or a mixture of both. As mentioned previously, if the nucleic acid is DNA, the leucine is encoded by a codon other than the CTG codon. If the nucleic acid is RNA, the leucine is encoded by a codon other than the CUG codon. In special cases where the nucleic acid is a mixture of DNA and RNA residues, the respective leucine residue is of course neither encoded by the CTG codon nor the CUG codon. In particularly preferred embodiments of the present invention the nucleic acid is DNA.

In DNA embodiments, the first leucine residue occurring on the N-terminal end of the encoded G-CSF is preferably encoded by a codon selected from the group of codons consisting of CTT, CTC, CTA, and TTA. The most preferred codon to encode said leucine residue is the TTA codon. In RNA embodiments, the first leucine residue occurring on the N-terminal end of the encoded G-CSF is preferably encoded by a codon selected from the group of codons consisting of CUU, CUC, CUA, and UUA. The most preferred codon to encode said leucine residue is then the UUA codon.

The sequence encoding granulocyte colony stimulating factor (G-CSF) comprised by the inventive nucleic acid may be optimized for a particular codon usage of a given host cell, e.g. to achieve faster translation rates and high accuracy. In particular, the sequence encoding granulocyte colony stimulating factor (G-CSF) comprised by the inventive nucleic acid may be optimized for codon usage of *E. coli*. "Codon optimized" as used herein, is intended to mean that a given nucleic acid coding sequence exhibits alterations vis-à-vis the native nucleic acid coding sequence (but without changing the encoded amino acid sequence). Said alterations match a more preferred codon usage in a host cell such as *E. coli*. Preferably, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or even 100% of the nucleic acid residues which can be codon optimized, are codon optimized, preferably for *E. coli*. In addition, codon optimized codons exhibit preferably the codon with the highest codon usage for the respective host cell. It is understood that codon optimisation as used herein is not allowed to give rise to a CTG/CUG codon for the first leucine residue occurring on the N-terminal end of the encoded G-CSF.

Nucleic acids according to the present invention may for example comprise a nucleic sequence selected from the group consisting of:

(SEQ ID NO: 9)
ACCCCC<u>CTT</u>GGCCCTGCCAGCTCCCTGCCC, (SEQ ID NO: 10)
ACCCCC<u>CTC</u>GGCCCTGCCAGCTCCCTGCCC, (SEQ ID NO: 11)
ACCCCC<u>CTA</u>GGCCCTGCCAGCTCCCTGCCC, (SEQ ID NO: 12)
ACCCCC<u>TTA</u>GGCCCTGCCAGCTCCCTGCCC, (SEQ ID NO: 13)
ACACCT<u>CTT</u>GGCCCTGCCAGCTCCCTGCCC, (SEQ ID NO: 14)
ACACCT<u>CTC</u>GGCCCTGCCAGCTCCCTGCCC,

```
                                            (SEQ ID NO: 15)
ACACCTCTAGGCCCTGCCAGCTCCCTGCCC, (SEQ ID NO: 16)
ACACCTTTAGGCCCTGCCAGCTCCCTGCCC, (SEQ ID NO: 17)
ACACCATTAGGTCCAGCTTCTTCTCTG
and (SEQ ID NO: 18)
ATGACACCATTAGGTCCAGCTTCTTCTCTG.
```

The above sequence stretches are located at the N-Terminus of G-CSF. Of these, SEQ ID NO: 16 and in particular SEQ ID NO: 17 and SEQ ID NO: 18 are particularly preferred. It is understood that for respective RNA embodiments the corresponding uracil-based nucleotides instead of the thymine-based nucleotides need to be considered and that each of said RNA sequences are specifically contemplated herein as well.

Furthermore, nucleic acids according to the present invention may for example comprise a nucleic sequence selected from the group consisting of SEQ ID NO: 19, SEQ ID NO: 20, SEQ ID NO: 21 and SEQ ID NO: 22 (all encoding natural human G-CSF according to SEQ ID NO: 6) or may be selected from the group consisting of SEQ ID NO: 23, SEQ ID NO: 24, SEQ ID NO: 25 and SEQ ID NO: 26 (all encoding recombinant human G-CSF according to SEQ ID NO: 5). Again the respective RNA sequences are specifically contemplated herein as well.

The nucleic acid according to the present invention does neither comprise the nucleic acid sequence according to SEQ ID NO: 1, nor according to SEQ ID NO: 2 (RNA equivalent of SEQ ID NO: 1), nor according to SEQ ID NO: 3, nor according to SEQ ID NO: 4 (RNA equivalent of SEQ ID NO: 3). More preferably, the nucleic acid according to the present invention does additionally neither comprise the nucleic acid sequence according to SEQ ID NO: 27 nor according to SEQ ID NO: 28 (RNA equivalent of SEQ ID NO: 27).

In order to enable production of G-CSF in a host cell of the invention, the nucleic acid of the invention may comprise elements operably linked to the sequence encoding G-CSF, which allow the transcription of the nucleic acid sequence and translation of the resulting mRNA into the encoded protein in a given host cell. In particular, the nucleic acid of the present invention may comprise a heterologous promoter. Said heterologous promoter may be operably linked to the nucleic acid sequence encoding the granulocyte colony stimulating factor (G-CSF), thereby providing for transcription of said nucleic acid sequence. A "heterologous promotor" for the nucleic acid encoding granulocyte colony stimulating factor (G-CSF) is a promoter, that is not found in direct association with the respective nucleic encoding granulocyte colony stimulating factor (G-CSF) in nature, i.e. is in nature not operably linked with the respective nucleic encoding granulocyte colony stimulating factor (G-CSF).

In a further aspect, the present invention relates to a nucleic acid 100% complementary to the aforementioned nucleic acid encoding human granulocyte colony stimulating factor (G-CSF), wherein the first leucine residue occurring on the N-terminal end of G-CSF is encoded by a codon other than the CTG/CUG codon, and wherein the nucleic acid does neither comprise the nucleic acid sequence according to SEQ ID NO: 1, nor according to SEQ ID NO: 2, nor according to SEQ ID NO: 3, nor according to SEQ ID NO: 4. 100% complementary implies in particular, that the respective (complementary) nucleic acid may not be 100% complementary to a nucleic acid sequence encoding granulocyte colony stimulating factor (G-CSF), wherein the first leucine residue occurring on the N-terminal end of G-CSF is encoded by a CTG or CUG codon.

In a further aspect the present invention relates to a vector comprising a nucleic acid according to the invention. The vector may for example be an expression vector or a cloning vector. The vector may also be a viral vector.

In a further aspect the present invention relates to a host cell comprising a nucleic acid and/or a vector according to the present invention. The host cell may be in particular a host cell suitable for recombinant production of proteins. The host cell may be a mammalian cell, such as a CHO cell, but may also be a bacterial cell such as an E. coli cell. E. coli cells are particularly preferred, if the nucleic acid according to the invention encodes recombinant human G-CSF. Furthermore, a host cell according to the present invention is preferably essentially free of group II truncations of G-CSF (see below). Particularly preferred is a host cell comprising recombinant G-CSF (SEQ ID NO: 5) but being essentially free of degradation products of recombinant G-CSF (SEQ ID NO: 5), in which the first 3 to first 7 amino acids of recombinant G-CSF (SEQ ID NO: 5) are absent.

In a further aspect, the present invention relates to a method for producing human G-CSF, the method comprising the following steps:
  a) expressing human G-CSF in a host cell according to the present invention,
  b) isolating said human G-CSF from said host cell, and
  c) optionally purifying said isolated human G-CSF.

It is particularly preferred if recombinant human G-CSF according to SEQ ID NO: 5 is produced with the method of the present invention. The host cell is preferably a prokaryotic host cell, such as an E. coli host cell.

The present invention also relates to a composition comprising human G-CSF, said composition being obtainable or obtained by a method according to the present invention.

In a further aspect the present invention relates to a composition comprising human G-CSF, wherein said human G-CSF comprises less than 0.5%, in particular less than 0.4% (w/w) human G-CSF impurities resulting from group II truncation products of said human G-CSF. As mentioned previously, human G-CSF contains a non-structured, flexible N-terminal region of about 10 amino acids length which is prone to degradation. The present invention divides the N-terminally truncated human G-CSF products into two groups. "Group I truncation products of G-CSF" are those truncated G-CSF products, which still exhibit at least one amino acid residue N-terminal of the first leucine residue occurring on the N-terminal end of G-CSF.

For natural human G-CSF (SEQ ID NO: 6) there is only one truncated polypeptide entity falling within the definition of "Group I truncation products of G-CSF", namely truncated G-CSF lacking the first amino acid of natural human G-CSF: T (threonine). The Group I truncation product of G-CSF according to SEQ ID NO: 6 is thus truncated by one amino acid at the N-terminus. For recombinant human G-CSF (SEQ ID NO: 5) there are two truncation products falling under the definition, namely the polypeptide species lacking the N-terminal methionine residue of recombinant human G-CSF (SEQ ID NO: 5) as well as the polypeptide species lacking the N-terminal methionine and threonine residues of recombinant human G-CSF. The Group I truncation products of G-CSF according to SEQ ID NO: 5 are thus truncated by one or two amino acids at the N-terminus.

With respect to G-CSF of SEQ ID NO: 8, said "group I truncations" lack the N-terminal residues (M) or (M)T of SEQ ID NO: 8. "(M)" in brackets is intended to reflect that SEQ ID NO: 8 anyway allows absence of the N-terminal methionine. The Group I truncation products of G-CSF according to SEQ ID NO: 8 are thus truncated by one or two amino acids at the N-terminus.

In contrast to "group I truncation products of G-CSF", "group II truncation products of G-CSF" lack up to 5 further amino acid residues (and not more) at the N-terminus of G-CSF. In other words, they lack all amino acids N-terminal of the first leucine residue occurring on the N-terminal end of G-CSF and lack 0 to 4 further amino acid residues (and not more) of the N-terminal amino acid residues of G-CSF.

With respect to natural human G-CSF (SEQ ID NO: 6), said "group II truncations" thus lack the N-terminal residues TP (SEQ ID NO: 29), TPL (SEQ ID NO: 30), TPLG (SEQ ID NO: 31), TPLGP (SEQ ID NO: 32), or TPLGPA (SEQ ID NO: 33) of SEQ ID NO: 6. The group II truncation products of G-CSF according to SEQ ID NO: 6 are thus truncated by two, three, four, five or six amino acids at the N-terminus. With respect to recombinant human G-CSF (SEQ ID NO: 5) this means that said "group II truncations" are truncated versions of recombinant G-CSF lacking the N-terminal sequence motifs MTP (SEQ ID NO: 34), MTPL (SEQ ID NO: 35), MTPLG (SEQ ID NO: 36), MTPLGP (SEQ ID NO: 37), or MTPLGPA (SEQ ID NO: 38) of SEQ ID NO: 5. The Group II truncation products of G-CSF according to SEQ ID NO: 6 are thus truncated by three, four, five, six or seven amino acids at the N-terminus. With respect to G-CSF of SEQ ID NO: 8, said "group II truncations" lack the N-terminal residues (M)TP (SEQ ID NO: 39), (M)TPL (SEQ ID NO: 40), (M)TPLG (SEQ ID NO: 41), (M)TPLGP (SEQ ID NO: 42), or (M)TPLGPA (SEQ ID NO: 43) of SEQ ID NO: 8. "(M)" is intended to reflect that SEQ ID NO: 8 anyway allows absence of the N-terminal methionine. The Group II truncation products of G-CSF according to SEQ ID NO: 8 are thus truncated by three, four, five, six or seven amino acids at the N-terminus.

It is understood that truncated G-CSF products lacking more amino acid residues at the N-terminus than specified for "group I truncation products of G-CSF", or "group II truncation products of G-CSF", respectively, do not fall within the respective groups.

It is also understood that wherever herein percentages of impurities resulting from truncation products of G-CSF are mentioned, that these percentages are given vis-à-vis the total content of G-CSF (non-truncated G-CSF+truncated impurities).

More preferably, the composition of the invention comprises less 0.38%, less than 0.36%, less than 0.35%, less than 0.34%, less than 0.32%, less than 0.3%, less than 0.28%, less than 0.26%, less than 0.25%, less than 0.24%, less than 0.22%, less than 0.20%, less than 0.18%, less than 0.16%, less than 0.15%, less than 0.12%, less than 0.10%, less than 0.08%, less than 0.06%, less than 0.05% or even 0.0% (i.e. below the detection limit of mass spectrometry) of said impurities resulting for group II truncation products of G-CSF.

The composition according to the present invention may comprises less than 0.3%, less than 0.28%, less than 0.26%, less than 0.25%, less than 0.24%, less than 0.22%, less than 0.20%, less than 0.18%, less than 0.16%, less than 0.15%, less than 0.12%, less than 0.10%, less than 0.08%, less than 0.06%, less than 0.05% or even 0.0% (i.e. below the detection limit of mass spectrometry) of the G-CSF truncation product lacking all amino acids N-terminal of the first leucine residue occurring on the N-terminal end of G-CSF and two further N-terminal amino acids (including the leucine residue).

This implicates that the composition according to the present invention may comprise less than 0.3%, less than 0.28%, less than 0.26%, less than 0.25%, less than 0.24%, less than 0.22%, less than 0.20%, less than 0.18%, less than 0.16%, less than 0.15%, less than 0.12%, less than 0.10%, less than 0.08%, less than 0.06%, less than 0.05% or even 0.0% (i.e. below the detection limit of mass spectrometry) of a G-CSF truncation product lacking:

i) the N-terminal sequence motif TPLG (SEQ ID NO: 31) for natural human G-CSF (SEQ ID NO: 6), i.e. lacking the first four N-terminal amino acids, ii) the N-terminal sequence motif MTPLG (SEQ ID NO: 36) for recombinant human G-CSF (SEQ ID NO: 5), i.e. lacking the first five N-terminal amino acids, or iii) lacking the N-terminal sequence motif (M)TPLG (SEQ ID NO: 41) for generic human G-CSF (SEQ ID NO: 8), i.e. lacking the first five N-terminal amino acids.

Likewise, the composition according to the present invention may comprise less than 0.10%, less than 0.09%, less than 0.08%, less than 0.07%, less than 0.06%, less than 0.05%, less than 0.04%, less than 0.03%, less than 0.02%, less than 0.01% or even 0.0% (i.e. below the detection limit of mass spectrometry) of a G-CSF truncation product lacking all amino acids N-terminal of the first leucine residue occurring on the N-terminal end of G-CSF and the leucine residue.

This means that the composition according to the present invention may comprise less than 0.10%, less than 0.09%, less than 0.08%, less than 0.07%, less than 0.06%, less than 0.05%, less than 0.04%, less than 0.03%, less than 0.02%, less than 0.01% or even 0.0% (i.e. below the detection limit of mass spectrometry) of a G-CSF truncation product lacking:

i) the N-terminal sequence motif TPL (SEQ ID NO: 30) for natural human G-CSF (SEQ ID NO: 6), i.e. lacking the first three N-terminal amino acids, ii) the N-terminal sequence motif MTPL (SEQ ID NO: 35) for recombinant human G-CSF (SEQ ID NO: 5), i.e. lacking the first four N-terminal amino acids, or iii) the N-terminal sequence motif (M)TPL (SEQ ID NO: 40) for generic human G-CSF SEQ ID NO: 8, i.e. lacking the first four N-terminal amino acids.

Likewise, the composition according to the present invention may comprises less than 0.10%, less than 0.09%, less than 0.08%, less than 0.07%, less than 0.06%, less than 0.05%, less than 0.04%, less than 0.03%, less than 0.02%, less than 0.01% or even 0.0% (i.e. below the detection limit of mass spectrometry) of a G-CSF truncation product lacking all amino acids N-terminal of the first leucine residue occurring on the N-terminal end of G-CSF and three further amino acids (including the leucine residue).

This means that the composition according to the present invention may comprise less than 0.10%, less than 0.09%, less than 0.08%, less than 0.07%, less than 0.06%, less than 0.05%, less than 0.04%, less than 0.03%, less than 0.02%, less than 0.01% or even 0.0% (i.e. below the detection limit of mass spectrometry) of a G-CSF truncation product lacking:

i) the N-terminal sequence motif TPLGP (SEQ ID NO: 32) for natural human G-CSF (SEQ ID NO: 6), i.e. lacking the first five N-terminal amino acids, ii) the N-terminal sequence motif MTPLGP (SEQ ID NO: 37) for recombinant human G-CSF (SEQ ID NO: 5), i.e. lacking the first six N-terminal amino acids, or iii) the N-terminal sequence motif (M)TPLGP (SEQ ID NO: 42) for generic human G-CSF SEQ ID NO: 8, i.e. lacking the first six N-terminal amino acids.

As the present invention affects in particular the abundance of group II truncation products in the composition, the composition according to the present invention may still comprise group I truncation products of G-CSF, as defined herein. The composition of the present invention may thus comprise for example up to 0.5%, up to 0.6%, up to 0.7%, up to 0.8%, up to 0.9%, up to 1.0%, up to 1.1%, up to 1.2%, up to 1.3%, up to 1.4%, or even up to 1.5% or more G-CSF truncation products exhibiting at least one amino acid N-terminal of the first leucine residue occurring on the N-terminal end of G-CSF.

This means that the composition according to the present invention may comprise for example up to 0.5%, up to 0.6%, up to 0.7%, up to 0.8%, up to 0.9%, up to 1.0%, up to 1.1%, up to 1.2%, up to 1.3%, up to 1.4%, or even up to 1.5% or more G-CSF truncation products lacking:
i) the N-terminal amino acid T for natural human G-CSF (SEQ ID NO: 6), i.e. lacking the first N-terminal amino acid,
ii) the N-terminal sequence motifs M or MT for recombinant human G-CSF (SEQ ID NO: 5), i.e. lacking the first or the first and the second N-terminal amino acid, or
iii) the N-terminal sequence motif (M) or (M)T for generic human G-CSF (SEQ ID NO: 8), i.e. lacking the first or the first and the second N-terminal amino acid.

The composition of the present invention may also be characterized by the ratio of the abundance of group II truncation products within the G-CSF fraction of the composition to the abundance of group I truncation products within the G-CSF fraction. Said ratio of group II truncation products to group I truncation products may be less than 0.3, preferably less than 0.2, more preferably less than 0.1, more preferably less than 0.05, more preferably less than 0.025, more preferably less than 0.01 or may most preferably be even 0.

The composition of the present invention may also be characterized by the ratio of the abundance of the truncation product lacking all amino acids N-terminal of the first leucine residue occurring on the N-terminal end of G-CSF and two further amino acids (including the leucine residue) within the G-CSF fraction of the composition to the abundance of group I truncation products within the G-CSF fraction. Said ratio of said truncation product to group I truncation products may be less than 0.2, more preferably less than 0.1, more preferably less than 0.05, more preferably less than 0.025, more preferably less than 0.01 or may most preferably be even 0.

This means that the ratio of:
a) the abundance of a G-CSF truncation product lacking:
  i) the N-terminal sequence motif TPLG (SEQ ID NO: 31) for natural human G-CSF (SEQ ID NO: 6), i.e. lacking the first four N-terminal amino acids,
  ii) the N-terminal sequence motif MTPLG (SEQ ID NO: 36) for recombinant human G-CSF (SEQ ID NO: 5), i.e. lacking the first five N-terminal amino acids, or
  iii) the N-terminal sequence motif (M)TPLG (SEQ ID NO: 41) for generic human G-CSF (SEQ ID NO: 8), i.e. lacking the first five N-terminal amino acids,
  to
b) the abundance of the respective group I truncation products of G-CSF, namely G-CSF truncation product lacking:
  iv) the N-terminal amino acid T for natural human G-CSF (SEQ ID NO: 6), i.e. lacking the first N-terminal amino acid,
  v) the N-terminal sequence motifs M and MT for recombinant human G-CSF (SEQ ID NO: 5), i.e. lacking the first or the first and the second N-terminal amino acid, or
  vi) the N-terminal sequence motifs (M) and (M)T for generic human G-CSF (SEQ ID NO: 8), i.e. lacking the first or the first and the second N-terminal amino acid,
  may be less than 0.2, more preferably less than 0.1, more preferably less than 0.05, more preferably less than 0.025, more preferably less than 0.01 or may most preferably be even 0.

The composition according to the present invention comprising human G-CSF may be for example a cell lysate, in particular a cell lysate of a host cell according to the present invention. However, the composition according to the present invention is most preferably a pharmaceutical composition comprising G-CSF and a pharmaceutically acceptable carrier, diluent and/or excipient.

In a further aspect, the present invention relates to a composition according to the present invention, in particular a pharmaceutical composition according to the present invention, for use in a method for the treatment of the human or animal body by therapy. In particular, the present invention relates a composition according to the present invention, in particular a pharmaceutical composition according to the present invention, for use in the treatment or prevention of neutropenia.

In a further aspect, the present invention relates to method of treatment of a subject suffering from neutropenia, the method comprising the step of administering a pharmaceutical composition according to the present invention to said subject in an effective amount.

In a further aspect, the present invention relates to a method of stimulating the survival, proliferation, differentiation, and function of neutrophil precursors and mature neutrophils in a subject in need thereof, the method comprising the step of administering a pharmaceutical composition according to the present invention to said subject in an effective amount.

In a further aspect, the present invention relates to a method of increasing the number of hematopoietic stem cells in the blood a subject, the method comprising the step of administering a pharmaceutical composition according to the present invention to said subject in an effective amount.

The term "comprising", as used herein, shall not be construed as being limited to the meaning "consisting of" (i.e. excluding the presence of additional other matter). Rather, "comprising" implies that optionally additional matter, features or steps may be present. The term "comprising" encompasses as particularly envisioned embodiments falling within its scope "consisting of" (i.e. excluding the presence of additional other matter) and "comprising but not consisting of" (i.e. requiring the presence of additional other matter, features or steps), with the former being more preferred.

The use of the word "a" or "an", when used herein, may mean "one," but it is also consistent with the meaning of "one or more," "at least one," and "one or more than one."

EXAMPLES

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Analysis of the Abundance of N-Terminal G-CSF Truncation Products in Three Different Commercial Products of Recombinant hG-CSF (Filgrastim)

Nine micrograms of respective filgrastim product were separated on a Zorbax 300SB-C18 column (4.6×150 mm, 3.5 μm particle size) with a gradient of solutions A (0.1% TFA in water) and B (0.1% TFA in ACN) at a flow rate of 1 ml/min: 25 min from 25% B to 54% B followed by a 32-min gradient from 54% B to 73% B. After UV and fluorescence detection, the flow was split 1:5 and then electrosprayed into the Exactive MS. For intact mass measurements the Exactive MS was operated with the following settings applied: spray voltage 4 kV, capillary temperature 275° C., sheath gas 20, aux gas 8, scan range 300-2,200 m/z, resolution ultra-high, AGC target 1e6, max inject time 100 ms, and microscans 10. Relative quantification of truncation products was performed based on the extracted ion chromatograms (EICs) of the native and the truncation products, respectively. Ion chromatograms were extracted in Xcalibur 2.1 using the theoretical masses of the +10 charged-molecules with a mass window of 0.5 Da.

Results are shown in FIG. 1 and additionally for two products in the table 1 below. The products contain between 0.7 and 1.3% group I truncations and between 0.5 and 0.6% group II truncations.

TABLE 1

| N-terminus of G-CSF and truncated variants | | | | | | | | Class | Sample 1 [%] | Sample 2 [%] |
|---|---|---|---|---|---|---|---|---|---|---|
| Met | Thr | Pro | Leu | Gly | Pro | Ala | Ser ... | — | 98.7 | 98.2 |
| | Thr | Pro | Leu | Gly | Pro | Ala | Ser ... | Group I | 0.5 | 0.5 |
| | | Pro | Leu | Gly | Pro | Ala | Ser ... | Group I | 0.2 | 0.8 |
| | | | Leu | Gly | Pro | Ala | Ser ... | Group II | 0.0 | 0.0 |
| | | | | Gly | Pro | Ala | Ser ... | Group II | 0.1 | 0.1 |
| | | | | | Pro | Ala | Ser ... | Group II | 0.4 | 0.3 |
| | | | | | | Ala | Ser ... | Group II | 0.1 | 0.1 |
| | | | | | | | Ser ... | Group II | 0.0 | 0.0 |

Example 2: Generation of a New Expression Vector for Recombinant hG-CSF

The silent mutation CTG to TTA was introduced into the plasmid pET9a-Fopt5 by mutation PCR. In brief, the insert was amplified by a PCR reaction (PCR1) using the primers Oligo 2761 TGCTAGTTATTGCTCAGCGGTGGCAG (SEQ ID NO: 44) und Oligo 2979 AGATATACATATGACACCATTAGGTCCAGCTTCTTCTCTG (SEQ ID NO: 45), Accu Prime Pfx polymerase (Invitrogen) and Accu Prime Pfx Reaction mix (Invitrogen) with the following PCR program: initial denaturation: 3 min 95° C., 25 cycles (30 sec 94° C., 30 sec 59° C., 1 min 68° C.) and final elongation for 7 min 68° C. Then, the integration PCR reaction (PCR2) was carried out as follows: 2 μL of the purified PCR product of PCR1 (insert) was combined with pET9a-Fopt5 and Phusion High-Fidelity Master Mix incl. HF buffer (Thermo Scientific) and subjected to the PCR program: 3 min 98° C., 25 cycles (20 sec 98° C., 30 sec 50° C., 2.5 min 72° C.) and final elongation for 7 min 72° C. After purification, the PCR product of PCR2 was subjected to a DpnI digestion.

Example 3: Analysis of the Abundance of N-Terminal G-CSF Truncation Products Depending on the Codon Used for L4 of Human Recombinant G-CSF Nine micrograms of filgrastim were separated on a Zorbax 300SB-C18 column (4.6×150 mm, 3.5 μm particle size) with a gradient of solutions A (0.1% TFA in water) and B (0.1% TFA in ACN) at a flow rate of 1 ml/min: 25 min from 25% B to 54% B followed by a 32-min gradient from 54% B to 73% B. After UV and fluorescence detection, the flow was split 1:5 and then electrosprayed into the Exactive MS. For intact mass measurements the Exactive MS was operated with the following settings applied: spray voltage 4 kV, capillary temperature 275° C., sheath gas 20, aux gas 8, scan range 300-2,200 m/z, resolution ultra-high, AGC target 1e6, max inject time 100 ms, and microscans 10. Relative quantification of truncation products was performed based on the extracted ion chromatograms (EICs) of the native and the truncation products, respectively. Ion chromatograms were extracted in Xcalibur 2.1 using the theoretical masses of the +10 charged-molecules with a mass window of 0.5 Da Results typically obtained with the modified nucleotide sequence are listed in table 2 below. The product contains 1.0% group I truncations and no group II truncations.

TABLE 2

| | | MS analysis in [%] | |
|---|---|---|---|
| N-terminus | Class | CTG codon | TTA codon |
| MTPLGPAS | — | 98.2 | 99.0 |
| TPLGPAS | Group I | 0.5 | 0.3 |
| PLGPAS | Group I | 0.8 | 0.7 |
| LGPAS | Group II | 0.0 | 0.0 |
| GPAS | Group II | 0.1 | 0.0 |
| PAS | Group II | 0.3 | 0.0 |
| AS | Group II | 0.1 | 0.0 |
| S | Group II | 0.0 | 0.0 |

Example 4: Yield Comparison for Human Recombinant G-CSF Depending on the Codon Used for L4

G-CSF yields of fermentations were analyzed by reversed-phase chromatography on harvest broth level. Fermentation samples were drawn at two time points post induction. Applying the strain with the modified codon the G-CSF output increased by 20% (n=3) or 50% (n=1), respectively, over the reference strain.

The invention claimed is:

1. Nucleic acid encoding human granulocyte-colony stimulating factor (G-CSF) according to SEQ ID NO: 8, wherein the first leucine residue occurring on the N-terminal end of the encoded G-CSF is L4 of SEQ ID NO: 8 and is encoded by a codon selected from the group of codons consisting of CTT, CTC, CTA, and TTA, and wherein the nucleic acid is DNA and does neither comprise the nucleic acid sequence according to SEQ ID NO: 1 nor according to SEQ ID NO: 3.

2. The nucleic acid according to claim 1, wherein the nucleic acid encodes hG-CSF according to SEQ ID NO: 5.

3. A nucleic acid 100% complementary to a nucleic acid according to claim 1.

4. The nucleic acid according to claim 1, wherein the sequence encoding G-CSF is codon-optimized.

5. A vector comprising a nucleic acid according to claim 1.

6. A host cell comprising a nucleic acid according any to claim 1.

7. The host cell according to claim 6, wherein the host cell is a bacterial cell.

8. A method for producing G-CSF, the method comprising the following steps:
   a) expressing G-CSF in a host cell according to claim 6,
   b) isolating G-CSF from said host cell, and
   c) optionally purifying said isolated G-CSF.

9. The nucleic acid according to claim 1, wherein the nucleic acid comprises a nucleic acid sequence selected from the group consisting of SEQ ID NOS. 9-18.

* * * * *

SEQUENCE LISTING

<160> NUMBER OF SEQ ID NOS: 45

<210> SEQ ID NO 1
<211> LENGTH: 96

```
<212> TYPE: DNA
<213> ORGANISM: Artificial sequence
<220> FEATURE:
<223> OTHER INFORMATION: Artificial sequence encoding part of human
      G-CSF

<400> SEQUENCE: 1
actccattag gtcctgcttc ttctctgccg caaagctttc tgctgaaatg tctggaacag    60
gttcgtaaaa tccagggtga cggtgctgca ctgcaa                              96

<210> SEQ ID NO 2
<211> LENGTH: 96
<212> TYPE: RNA
<213> ORGANISM: Artificial sequence
<220> FEATURE:
<223> OTHER INFORMATION: Artificial sequence encoding part of human
      G-CSF

<400> SEQUENCE: 2
acuccauuag guccugcuuc uucucugccg caaagcuuuc ugcugaaaug ucuggaacag    60
guucguaaaa uccaggguga cggugcugca cugcaa                              96

<210> SEQ ID NO 3
<211> LENGTH: 96
<212> TYPE: DNA
<213> ORGANISM: Artificial sequence
<220> FEATURE:
<223> OTHER INFORMATION: Artificial sequence encoding part of human
      G-CSF

<400> SEQUENCE: 3
actccattag gtccagcttc ctctctgccg caaagcttcc tgctgaaatg cctggaacag    60
gttcgtaaaa tccagggtga tggtgctgct ctgcag                              96

<210> SEQ ID NO 4
<211> LENGTH: 96
<212> TYPE: RNA
<213> ORGANISM: Artificial sequence
<220> FEATURE:
<223> OTHER INFORMATION: Artificial sequence encoding part of human
      G-CSF

<400> SEQUENCE: 4
acuccauuag guccagcuuc cucucugccg caaagcuucc ugcugaaaug ccuggaacag    60
guucguaaaa uccaggguga uggugcugcu cugcag                              96

<210> SEQ ID NO 5
<211> LENGTH: 175
<212> TYPE: PRT
<213> ORGANISM: Artificial sequence
<220> FEATURE:
<223> OTHER INFORMATION: Recombinant form of human G-CSF with N-terminal
      methionine

<400> SEQUENCE: 5

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60
```

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 6
<211> LENGTH: 174
<212> TYPE: PRT
<213> ORGANISM: Homo sapiens

<400> SEQUENCE: 6

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
                20                  25                  30

Glu Lys Leu Cys Ala Thr Tyr Lys Leu Cys His Pro Glu Glu Leu Val
            35                  40                  45

Leu Leu Gly His Ser Leu Gly Ile Pro Trp Ala Pro Leu Ser Ser Cys
        50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
            130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 7
<211> LENGTH: 204
<212> TYPE: PRT
<213> ORGANISM: Homo sapiens

<400> SEQUENCE: 7

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
            50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                    85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
                115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
                195                 200

<210> SEQ ID NO 8
<211> LENGTH: 175
<212> TYPE: PRT
<213> ORGANISM: Artificial sequence
<220> FEATURE:
<223> OTHER INFORMATION: Consensus sequence comprising sequence of
      natural human as well as recombinant human G-CSF
<220> FEATURE:
<221> NAME/KEY: MISC_FEATURE
<222> LOCATION: (1)..(1)
<223> OTHER INFORMATION: Xaa may be Met or absent

<400> SEQUENCE: 8

Xaa Thr Pro Leu Gly Pro Ala Ser Ser Leu Pro Gln Ser Phe Leu Leu
 1                   5                  10                  15

Lys Cys Leu Glu Gln Val Arg Lys Ile Gln Gly Asp Gly Ala Ala Leu
                20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
 50                  55                  60

Cys Pro Ser Gln Ala Leu Gln Leu Ala Gly Cys Leu Ser Gln Leu His
 65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 9
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTT codon instead of CTG for first leucine

<400> SEQUENCE: 9
accccccttg gccctgccag ctccctgccc                                          30

<210> SEQ ID NO 10
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTC codon instead of CTG for first leucine

<400> SEQUENCE: 10
acccccctcg gccctgccag ctccctgccc                                          30

<210> SEQ ID NO 11
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTA codon instead of CTG for first leucine

<400> SEQUENCE: 11
acccccctag gccctgccag ctccctgccc                                          30

<210> SEQ ID NO 12
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but TTA codon instead of CTG for first leucine

<400> SEQUENCE: 12 accccccttag gccctgccag ctccctgccc                                         30

<210> SEQ ID NO 13
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTT codon instead of CTG for first leucine

<400> SEQUENCE: 13
acacctcttg gccctgccag ctccctgccc                                          30

<210> SEQ ID NO 14
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTC codon instead of CTG for first leucine

<400> SEQUENCE: 14
acacctctcg gccctgccag ctccctgccc                                          30

```
<210> SEQ ID NO 15
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but CTA codon instead of CTG for first leucine

<400> SEQUENCE: 15
acacctctag gccctgccag ctccctgccc                                          30

<210> SEQ ID NO 16
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of hG-CSF, but TTA codon instead of CTG for first leucine

<400> SEQUENCE: 16 acaccthag gccctgccag ctccctgccc                                           30

<210> SEQ ID NO 17
<211> LENGTH: 27
<212> TYPE: DNA
<213> ORGANISM: Artificial sequence
<220> FEATURE:
<223> OTHER INFORMATION: nucleic acid sequence encoding amino acids 1-9
      of hG-CSF, but TTA codon instead of CTG for first leucine

<400> SEQUENCE: 17
acaccattag gtccagcttc ttctctg                                             27

<210> SEQ ID NO 18
<211> LENGTH: 30
<212> TYPE: DNA
<213> ORGANISM: Artificial sequence
<220> FEATURE:
<223> OTHER INFORMATION: nucleic acid sequence encoding amino acids 1-10
      of recombinant hG-CSF, but TTA codon instead of CTG for first
      leucine

<400> SEQUENCE: 18
atgacaccat taggtccagc ttcttctctg                                          30

<210> SEQ ID NO 19
<211> LENGTH: 522
<212> TYPE: DNA
<213> ORGANISM: Artificial sequence
<220> FEATURE:
<223> OTHER INFORMATION: nucleic acid sequence encoding hG-CSF, but CTT
      codon instead of CTG for first leucine

<400> SEQUENCE: 19
accccccttg gccctgccag ctccctgccc cagagcttcc tgctcaagtg cttagagcaa         60
gtgaggaaga tccagggcga tggcgcagcg ctccaggaga agctgtgtgc cacctacaag        120
ctgtgccacc ccgaggagct ggtgctgctc ggacactctc tgggcatccc ctgggctccc        180
ctgagcagct gccccagcca ggccctgcag ctgcaggct gcttgagcca actccatagc         240
ggccttttcc tctaccaggg gctcctgcag gccctggaag gatctccccc cgagttgggt        300
cccaccttgg acacactgca gctggacgtc gccgactttg ccaccaccat ctggcagcag        360
atggaagaac tgggaatggc ccctgccctg cagcccaccc agggtgccat gccggccttc        420
gcctctgctt tccagcgccg ggcaggaggg gtcctagttg cctcccatct gcagagcttc        480
```
ctggaggtgt cgtaccgcgt tctacgccac cttgcccagc cc        522

<210> SEQ ID NO 20
<211> LENGTH: 522
<212> TYPE: DNA
<213> ORGANISM: Artificial sequence
<220> FEATURE:
<223> OTHER INFORMATION: nucleic acid sequence encoding hG-CSF, but CTC
      codon instead of CTG for first leucine

<400> SEQUENCE: 20 accccctcg gccctgccag ctccctgccc cagagcttcc tgctcaagtg cttagagcaa        60
gtgaggaaga tccagggcga tggcgcagcg ctccaggaga agctgtgtgc cacctacaag       120
ctgtgccacc ccgaggagct ggtgctgctc ggacactctc tgggcatccc ctgggctccc       180
ctgagcagct gccccagcca ggccctgcag ctggcaggct gcttgagcca actccatagc       240
ggccttttcc tctaccaggg gctcctgcag gccctggaag ggatctcccc cgagttgggt       300
cccaccttgg acacactgca gctggacgtc gccgactttg ccaccaccat ctggcagcag       360
atggaagaac tgggaatggc ccctgccctg cagcccaccc agggtgccat gccggccttc       420
gcctctgctt tccagcgccg ggcaggaggg gtcctagttg cctcccatct gcagagcttc       480
ctggaggtgt cgtaccgcgt tctacgccac cttgcccagc cc        522

<210> SEQ ID NO 21
<211> LENGTH: 522
<212> TYPE: DNA
<213> ORGANISM: Artificial Sequence
<220> FEATURE:
<223> OTHER INFORMATION: nucleic acid sequence encoding hG-CSF, but CTA
      codon instead of CTG for first leucine

<400> SEQUENCE: 21 accccctag gccctgccag ctccctgccc cagagcttcc tgctcaagtg cttagagcaa         60
gtgaggaaga tccagggcga tggcgcagcg ctccaggaga agctgtgtgc cacctacaag       120
ctgtgccacc ccgaggagct ggtgctgctc ggacactctc tgggcatccc ctgggctccc       180
ctgagcagct gccccagcca ggccctgcag ctggcaggct gcttgagcca actccatagc       240
ggccttttcc tctaccaggg gctcctgcag gccctggaag ggatctcccc cgagttgggt       300
cccaccttgg acacactgca gctggacgtc gccgactttg ccaccaccat ctggcagcag       360
atggaagaac tgggaatggc ccctgccctg cagcccaccc agggtgccat gccggccttc       420
gcctctgctt tccagcgccg ggcaggaggg gtcctagttg cctcccatct gcagagcttc       480
ctggaggtgt cgtaccgcgt tctacgccac cttgcccagc cc        522

<210> SEQ ID NO 22
<211> LENGTH: 522
<212> TYPE: DNA
<213> ORGANISM: Artificial Sequence
<220> FEATURE:
<223> OTHER INFORMATION: nucleic acid sequence encoding hG-CSF, but TTA
      codon instead of CTG for first leucine

<400> SEQUENCE: 22 accccttag gccctgccag ctccctgccc cagagcttcc tgctcaagtg cttagagcaa         60
gtgaggaaga tccagggcga tggcgcagcg ctccaggaga agctgtgtgc cacctacaag       120
ctgtgccacc ccgaggagct ggtgctgctc ggacactctc tgggcatccc ctgggctccc       180
ctgagcagct gccccagcca ggccctgcag ctggcaggct gcttgagcca actccatagc       240

```
ggcctttcc tctaccaggg gctcctgcag gccctggaag ggatctcccc cgagttgggt    300
cccaccttgg acacactgca gctggacgtc gccgactttg ccaccaccat ctggcagcag    360
atggaagaac tgggaatggc ccctgccctg cagcccaccc agggtgccat gccggccttc    420
gcctctgctt ccagcgccg gcaggaggg gtcctagttg cctcccatct gcagagcttc    480
ctggaggtgt cgtaccgcgt tctacgccac cttgcccagc cc                       522
```

```
<210> SEQ ID NO 23
<211> LENGTH: 525
<212> TYPE: DNA
<213> ORGANISM: Artificial sequence
<220> FEATURE:
<223> OTHER INFORMATION: nucleic acid sequence encoding recombinant
      hG-CSF, but CTT codon instead of CTG for first leucine

<400> SEQUENCE: 23
```

```
atgaccccc ttggccctgc agctccctg ccccagagct tcctgctcaa gtgcttagag      60
caagtgagga agatccaggg cgatggcgca gcgctccagg agaagctgtg tgccacctac   120
aagctgtgcc accccgagga gctggtgctg ctcggacact ctctgggcat cccctgggct   180
cccctgagca gctgccccag ccaggccctg cagctggcag gctgcttgag ccaactccat   240
agcggccttt tcctctacca ggggctcctg caggccctgg aagggatctc cccgagttg    300 ggtcccacct tggacacact gcagctggac gtcgccgact ttgccaccac catctggcag   360
cagatggaag aactgggaat ggcccctgcc ctgcagccca cccagggtgc catgccggcc   420
ttcgcctctg ctttccagcg ccgggcagga ggggtcctag ttgcctccca tctgcagagc   480
ttcctggagg tgtcgtaccg cgttctacgc caccttgccc agccc                   525
```

```
<210> SEQ ID NO 24
<211> LENGTH: 525
<212> TYPE: DNA
<213> ORGANISM: Artificial sequence
<220> FEATURE:
<223> OTHER INFORMATION: nucleic acid sequence encoding recombinant
      hG-CSF, but CTC codon instead of CTG for first leucine

<400> SEQUENCE: 24
```

```
atgaccccc tcggccctgc agctccctg ccccagagct tcctgctcaa gtgcttagag      60
caagtgagga agatccaggg cgatggcgca gcgctccagg agaagctgtg tgccacctac   120
aagctgtgcc accccgagga gctggtgctg ctcggacact ctctgggcat cccctgggct   180
cccctgagca gctgccccag ccaggccctg cagctggcag gctgcttgag ccaactccat   240
agcggccttt tcctctacca ggggctcctg caggccctgg aagggatctc cccgagttg    300 ggtcccacct tggacacact gcagctggac gtcgccgact ttgccaccac catctggcag   360
cagatggaag aactgggaat ggcccctgcc ctgcagccca cccagggtgc catgccggcc   420
ttcgcctctg ctttccagcg ccgggcagga ggggtcctag ttgcctccca tctgcagagc   480
ttcctggagg tgtcgtaccg cgttctacgc caccttgccc agccc                   525
```

```
<210> SEQ ID NO 25
<211> LENGTH: 525
<212> TYPE: DNA
<213> ORGANISM: Artificial sequence
<220> FEATURE:
<223> OTHER INFORMATION: nucleic acid sequence encoding recombinant
      hG-CSF, but CTA codon instead of CTG for first leucine

<400> SEQUENCE: 25
```

```
atgacccccc taggccctgc cagctccctg ccccagagct tcctgctcaa gtgcttagag      60
caagtgagga agatccaggg cgatggcgca gcgctccagg agaagctgtg tgccacctac     120
aagctgtgcc accccgagga gctggtgctg ctcggacact ctctgggcat ccctgggct     180 cccctgagca gctgccccag ccaggccctg cagctggcag gctgcttgag ccaactccat     240
agcggccttt tcctctacca ggggctcctg caggccctgg aagggatctc ccccgagttg     300
ggtcccacct tggacacact gcagctggac gtcgccgact ttgccaccac catctggcag     360
cagatggaag aactgggaat ggcccctgcc ctgcagccca cccagggtgc catgccggcc     420
ttcgcctctg ctttccagcg ccgggcagga ggggtcctag ttgcctccca tctgcagagc     480
ttcctggagg tgtcgtaccg cgttctacgc caccttgccc agccc                    525
```

<210> SEQ ID NO 26
<211> LENGTH: 525
<212> TYPE: DNA
<213> ORGANISM: Artificial sequence
<220> FEATURE:
<223> OTHER INFORMATION: nucleic acid sequence encoding recombinant
      hG-CSF, but TTA codon instead of CTG for first leucine

<400> SEQUENCE: 26

```
atgacccccct taggccctgc cagctccctg ccccagagct tcctgctcaa gtgcttagag     60
caagtgagga agatccaggg cgatggcgca gcgctccagg agaagctgtg tgccacctac    120
aagctgtgcc accccgagga gctggtgctg ctcggacact ctctgggcat ccctgggct    180 cccctgagca gctgccccag ccaggccctg cagctggcag gctgcttgag ccaactccat    240
agcggccttt tcctctacca ggggctcctg caggccctgg aagggatctc ccccgagttg    300
ggtcccacct tggacacact gcagctggac gtcgccgact ttgccaccac catctggcag    360
cagatggaag aactgggaat ggcccctgcc ctgcagccca cccagggtgc catgccggcc    420
ttcgcctctg ctttccagcg ccgggcagga ggggtcctag ttgcctccca tctgcagagc    480
ttcctggagg tgtcgtaccg cgttctacgc caccttgccc agccc                   525
```

<210> SEQ ID NO 27
<211> LENGTH: 12
<212> TYPE: DNA
<213> ORGANISM: Artificial sequence
<220> FEATURE:
<223> OTHER INFORMATION: Artificial sequence encoding N-terminus of
      human G-CSF

<400> SEQUENCE: 27
actccattag gt                                                        12

<210> SEQ ID NO 28
<211> LENGTH: 12
<212> TYPE: RNA
<213> ORGANISM: Artificial sequence
<220> FEATURE:
<223> OTHER INFORMATION: Artificial sequence encoding N-terminus of
      human G-CSF

<400> SEQUENCE: 28
acuccauuag gu                                                        12

<210> SEQ ID NO 29
<211> LENGTH: 2
<212> TYPE: PRT
<213> ORGANISM: Homo sapiens

```
<400> SEQUENCE: 29

Thr Pro
1

<210> SEQ ID NO 30
<211> LENGTH: 3
<212> TYPE: PRT
<213> ORGANISM: Homo sapiens

<400> SEQUENCE: 30

Thr Pro Leu
1

<210> SEQ ID NO 31
<211> LENGTH: 4
<212> TYPE: PRT
<213> ORGANISM: Homo sapiens

<400> SEQUENCE: 31

Thr Pro Leu Gly
1

<210> SEQ ID NO 32
<211> LENGTH: 5
<212> TYPE: PRT
<213> ORGANISM: Homo sapiens

<400> SEQUENCE: 32

Thr Pro Leu Gly Pro
1               5

<210> SEQ ID NO 33
<211> LENGTH: 6
<212> TYPE: PRT
<213> ORGANISM: Homo sapiens

<400> SEQUENCE: 33

Thr Pro Leu Gly Pro Ala
1               5

<210> SEQ ID NO 34
<211> LENGTH: 3
<212> TYPE: PRT
<213> ORGANISM: Artificial sequence
<220> FEATURE:
<223> OTHER INFORMATION: 3 N-terminal amino acids of recombinant G-CSF

<400> SEQUENCE: 34

Met Thr Pro
1

<210> SEQ ID NO 35
<211> LENGTH: 4
<212> TYPE: PRT
<213> ORGANISM: Artificial Sequence
<220> FEATURE:
<223> OTHER INFORMATION: 4 N-terminal amino acids of recombinant G-CSF

<400> SEQUENCE: 35

Met Thr Pro Leu
1

<210> SEQ ID NO 36
<211> LENGTH: 5
<212> TYPE: PRT
```

```
<213> ORGANISM: Artificial Sequence
<220> FEATURE:
<223> OTHER INFORMATION: 5 N-terminal amino acids of recombinant G-CSF

<400> SEQUENCE: 36

Met Thr Pro Leu Gly
1               5

<210> SEQ ID NO 37
<211> LENGTH: 6
<212> TYPE: PRT
<213> ORGANISM: Artificial Sequence
<220> FEATURE:
<223> OTHER INFORMATION: 6 N-terminal amino acids of recombinant G-CSF

<400> SEQUENCE: 37

Met Thr Pro Leu Gly Pro
1               5

<210> SEQ ID NO 38
<211> LENGTH: 7
<212> TYPE: PRT
<213> ORGANISM: Artificial Sequence
<220> FEATURE:
<223> OTHER INFORMATION: 7 N-terminal amino acids of recombinant G-CSF

<400> SEQUENCE: 38

Met Thr Pro Leu Gly Pro Ala
1               5

<210> SEQ ID NO 39
<211> LENGTH: 3
<212> TYPE: PRT
<213> ORGANISM: Artificial sequence
<220> FEATURE:
<223> OTHER INFORMATION: Consensus sequence comprising N-terminal
      sequence of natural human as well as recombinant human G-CSF
<220> FEATURE:
<221> NAME/KEY: MISC_FEATURE
<222> LOCATION: (1)..(1)
<223> OTHER INFORMATION: Xaa may be Met or absent

<400> SEQUENCE: 39

Xaa Thr Pro
1

<210> SEQ ID NO 40
<211> LENGTH: 4
<212> TYPE: PRT
<213> ORGANISM: Artificial Sequence
<220> FEATURE:
<223> OTHER INFORMATION: Consensus sequence comprising N-terminal
      sequence of natural human as well as recombinant human G-CSF
<220> FEATURE:
<221> NAME/KEY: MISC_FEATURE
<222> LOCATION: (1)..(1)
<223> OTHER INFORMATION: Xaa may be Met or absent

<400> SEQUENCE: 40

Xaa Thr Pro Leu
1

<210> SEQ ID NO 41
<211> LENGTH: 5
<212> TYPE: PRT
<213> ORGANISM: Artificial Sequence
<220> FEATURE:
<223> OTHER INFORMATION: Consensus sequence comprising N-terminal
      sequence of natural human as well as recombinant human G-CSF
```

```
<220> FEATURE:
<221> NAME/KEY: MISC_FEATURE
<222> LOCATION: (1)..(1)
<223> OTHER INFORMATION: Xaa may be Met or absent

<400> SEQUENCE: 41

Xaa Thr Pro Leu Gly
1               5

<210> SEQ ID NO 42
<211> LENGTH: 6
<212> TYPE: PRT
<213> ORGANISM: Artificial Sequence
<220> FEATURE:
<223> OTHER INFORMATION: Consensus sequence comprising N-terminal
      sequence of natural human as well as recombinant human G-CSF
<220> FEATURE:
<221> NAME/KEY: MISC_FEATURE
<222> LOCATION: (1)..(1)
<223> OTHER INFORMATION: Xaa may be Met or absent

<400> SEQUENCE: 42

Xaa Thr Pro Leu Gly Pro
1               5

<210> SEQ ID NO 43
<211> LENGTH: 7
<212> TYPE: PRT
<213> ORGANISM: Artificial Sequence
<220> FEATURE:
<223> OTHER INFORMATION: Consensus sequence comprising N-terminal
      sequence of natural human as well as recombinant human G-CSF
<220> FEATURE:
<221> NAME/KEY: MISC_FEATURE
<222> LOCATION: (1)..(1)
<223> OTHER INFORMATION: Xaa may be Met or absent

<400> SEQUENCE: 43

Xaa Thr Pro Leu Gly Pro Ala
1               5

<210> SEQ ID NO 44
<211> LENGTH: 26
<212> TYPE: DNA
<213> ORGANISM: Artificial sequence
<220> FEATURE:
<223> OTHER INFORMATION: Primer: Oligo 2761

<400> SEQUENCE: 44
tgctagttat tgctcagcgg tggcag                                          26

<210> SEQ ID NO 45
<211> LENGTH: 40
<212> TYPE: DNA
<213> ORGANISM: Artificial Sequence
<220> FEATURE:
<223> OTHER INFORMATION: Primer: Oligo 2979

<400> SEQUENCE: 45
agatatacat atgacaccat taggtccagc ttcttctctg                           40
```